(12) United States Patent
Erdem et al.

(10) Patent No.: US 8,071,710 B2
(45) Date of Patent: Dec. 6, 2011

(54) THERMOPLASTIC POLYPHENOXYQUINOXALINE AND METHOD OF PREPARING THE SAME

(75) Inventors: Haci Bayram Erdem, Akron, OH (US); Frank Wayne Harris, Boca Raton, FL (US)

(73) Assignee: The University of Akron, Akron, OH (US)

( * ) Notice: Subject to any disclaimer, the term of this patent is extended or adjusted under 35 U.S.C. 154(b) by 14 days.

(21) Appl. No.: 12/543,936

(22) Filed: Aug. 19, 2009

(65) Prior Publication Data

US 2010/0048857 A1   Feb. 25, 2010

Related U.S. Application Data

(60) Provisional application No. 61/089,926, filed on Aug. 19, 2008.

(51) Int. Cl.
*C08G 8/02* (2006.01)

(52) U.S. Cl. ........................................ 528/125; 528/128

(58) Field of Classification Search .................. 528/125, 528/128

See application file for complete search history.

(56) References Cited

U.S. PATENT DOCUMENTS

| | | | |
|---|---|---|---|
| 3,852,244 A | 12/1974 | Heath et al. | |
| 3,956,238 A | 5/1976 | Heath et al. | |
| 4,108,837 A | 8/1978 | Johnson et al. | |
| 4,788,271 A | 11/1988 | Hergenrother et al. | |
| 4,908,426 A | 3/1990 | Hergenrother et al. | |
| 4,914,177 A | 4/1990 | Fang | |
| 5,010,197 A | 4/1991 | Hergenrother et al. | |
| 5,030,704 A | 7/1991 | Harris et al. | |
| 5,229,482 A | 7/1993 | Brunelle | |

FOREIGN PATENT DOCUMENTS

CA   847963   7/1970

OTHER PUBLICATIONS

Heterocycle-Activated Aromatic Nucleophilic Substitution: Poly(aryl ether phenylquinoxalines) by J. Hedrick, R. Twieg, T. Matray, and K. Carter; Macromolecules, vol. 26, No. 18 (1993), pp. 4833-4839.
Poly(aryl ether-phenylquinoxalines) by James L Hedrick and Jeff W. Labadie; Macromolecules, vol. 23, No. 6 (Mar. 19, 1990), pp. 1561-1568.
J. Hedrick et al., Heterocycle-Activated Aromatic Nucleophilic Substitution: Poly(aryl ether phenylquinoxalines). 2, Macromolecules, 1993, pp. 4833-4839, vol. 26, No. 18, American Chemical Society.
James L. Hedrick et al., Poly(aryl ether-phenylquinoxalines), Macromolecules, 1990, pp. 1561-1568, vol. 23, No. 6, American Chemical Society.

*Primary Examiner* — Terressa Boykin
(74) *Attorney, Agent, or Firm* — Renner, Kenner, Greive, Bobak, Taylor & Weber

(57) ABSTRACT

The manufacture of polyetherquinoxalines may be accomplished by polymerization of quinoxaline and related monomers with a bisphenol under aromatic nucleophilic substitution reaction conditions. A method of manufacture includes contacting a substituted or unsubstituted quinoxaline having replaceable groups at the 2,3 positions with a bisphenol or a bisphenol derivative under aromatic nucleophilic substitution reaction conditions. The resulting polyetherquinoxalines contain quinoxaline groups joined by ether linkages at the 2 and 3 positions of the quinoxaline groups. In one example, the polyetherquinoxaline has a formula represented as

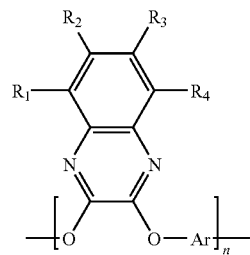

wherein "n" is an integer from 1 to 10000, and $R_1$, $R_2$, $R_3$, $R_4$ are independently hydrogen, methyl, $CF_3$, tert-butyl, benzoyl, benzenesulfonyl, a sulfonic acid salt, an aliphatic group, an alicyclic group, or an aryl group, and Ar is an aromatic radical. These melt-processable polyetherquinoxalines can be prepared under relatively mild conditions, have excellent thermal and mechanical properties, and are organo-soluble, transparent and colorless thermoplastics.

20 Claims, No Drawings

THERMOPLASTIC POLYPHENOXYQUINOXALINE AND METHOD OF PREPARING THE SAME

CROSS REFERENCE TO RELATED APPLICATIONS

This application claims benefit of U.S. Provisional Patent Application No. 61/089,926 filed on Aug. 19, 2008, now abandoned.

BACKGROUND OF THE INVENTION

The present invention relates to new polyether quinoxalines, which may be used in aerospace, automotive, microelectronic, optical, membrane applications such as gas separation membranes and molecular separation membranes.

Polyquinoxalines are a well established class of high performance thermoplastics with proven potential in aerospace, microelectronic and membrane applications.

Previous types of polyquinoxalines and polyphenylquinoxalines are normally prepared by the reaction of bis-alpha-carbonyl compounds with an organic tetramine, but other synthesis methods are also known.

Methods of synthesis of polyquinoxalines include the condensation of 1,4-diglyoxalylbenzene dehydrate with 3,3'-diaminobenzidine. The preparation of polyphenylquinoxalines by the reaction of combinations of two tetraamines, 3,3'-diaminobenzidine and 3,3',4,4'-tetraminodiphenyl ether, with two bisbenzils, 4,4'-dibenzil and 4,4'-oxydibenzil is also known.

The formation of certain moldable polyetherquinoxalines from a wide variety of bis-alpha-carbonyl compounds and aromatic organic tetramines has been described, as has been the formation of polyphenylquinoxalines containing alkylenedioxy groups. These polymers have relatively lower glass transition and melt viscosity than other previously reported polyquinoxalines. As a result, they have better melt processability than the previously reported polyquinoxalines. But they still require the synthesis of tetramines and tetraketones.

A common organic tetramine, 3,3'-diaminobenzidine is commercially available but expensive and toxic. Aromatic tetraketones are not commercially available and require successive chemical steps to prepare, further increasing cost of the polyquinoxalines.

The preparation of polyquinoxaline by self condensation of a monomer having both a 1,2-diketone and a 1,2-primary diamine in the molecule has been described. Preparation of this monomer, 3,4-diaminobenzil, requires successive chemical steps and relatively expensive starting materials such as phenyl acetylene and palladium acetate.

Generally, polymerizations by aromatic nucleophilic substitution reaction to synthesize a polyarylether, where formation of the ether linkage is the polymer forming reaction, are well known in the art. Many commercially available melt-processable polyarylethers, such as polysulfones, polyetheretherketones or polyetherimides are prepared under aromatic nucleophilic substitution conditions in a polar aprotic solvent. Optimally, solvents used should be able to dissolve monomers, growing chains, and the final polymer at the polymerization temperature. Polar aprotic solvents such as dimethylsulfoxide, dimethylacetamide, dimethylformamide, n-methylpyrrolidinone, sulfolane and diphenylsulfone are generally used. A polymerization solvent should optimally be substantially free of water and the reaction is run under an inert gas atmosphere, such as nitrogen or argon. This polymerization can be performed using a single step process or a two step process, or using a heterogeneous two step process using a phase transfer catalyst.

In the single step process, a bisphenol and activated dihalide or dinitro monomer are polymerized in a polar aprotic solvent using an alkali metal salt, preferably potassium carbonate or sodium carbonate. In the single step process, potassium carbonate reacts with the phenol groups and forms reactive phenoxide salt and potassium bicarbonate. Over the range of 100-200° C., 2 moles of potassium bicarbonate decompose into 1 mole of carbon dioxide, 1 mole of potassium carbonate and 1 mole of water.

In the two step process, bisphenol is converted to a double alkali metal salt first, and then reacted with about stoichiometric quantities of activated dihalide or dinitro monomer. Polyarylethers can also be synthesized by a heterogeneous aromatic nucleophilic substitution reaction in relatively nonpolar solvents such as o-dichlorobenzene, using a phase transfer catalyst having sufficient thermal stability under the polymerization conditions.

The preparation of other polyphenylquinoxalines by reacting bis-hydroxyphenylquinoxalines with activated difluoro monomers under aromatic nucleophilic substitution reaction conditions has also been disclosed. Preparation of bis(hydroxyphenylquinoxalines) requires successive chemicals steps and the activated difluoro monomers are expensive.

The formation of certain polyphenylquinoxalines by reacting bis-fluoro-poly-phenylated-quinoxalines with various bis-hydroxylated aromatic compounds under aromatic nucleophilic substitution reaction conditions is also known. The synthetic routes described eliminate the need for tetramines but still require expensive fluorinated starting materials as well as relatively high number of steps to synthesize the monomers.

Other polyether quinoxalines may be synthesized from a self-polymerizable mixture of monomers by a route that eliminates the need for the synthesis of tetraketones. However, that method still requires the use of expensive 4-fluoro-1,2-phenylenediamine and a high number of chemical steps.

Thus, it appears highly desirable to manufacture melt-processable polyetherquinoxalines from low cost starting materials.

BRIEF SUMMARY OF THE INVENTION

It is an aspect of this invention to provide melt-processable polyetherquinoxalines comprising a plurality of quinoxaline groups joined by ether linkages at the 2 and 3 positions of the quinoxaline groups.

In one example of the present invention, a polyetherquinoxaline with a structure shown in Formula I is provided.

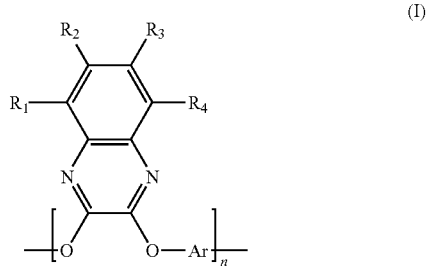

(I)

Still another aspect of the invention is to provide a method for synthesizing a polyetherquinoxaline, where the method includes contacting a substituted or unsubstituted quinoxaline having replaceable groups at the 2,3 positions with a bisphenol or a derivative thereof under aromatic nucleophilic substitution reaction conditions.

A further aspect of this invention is to provide a usable process to manufacture a polyetherquinoxaline by the reaction of the monomer shown in Formula II with a bisphenol or bisphenol derivative as shown in the reaction of Formula III.

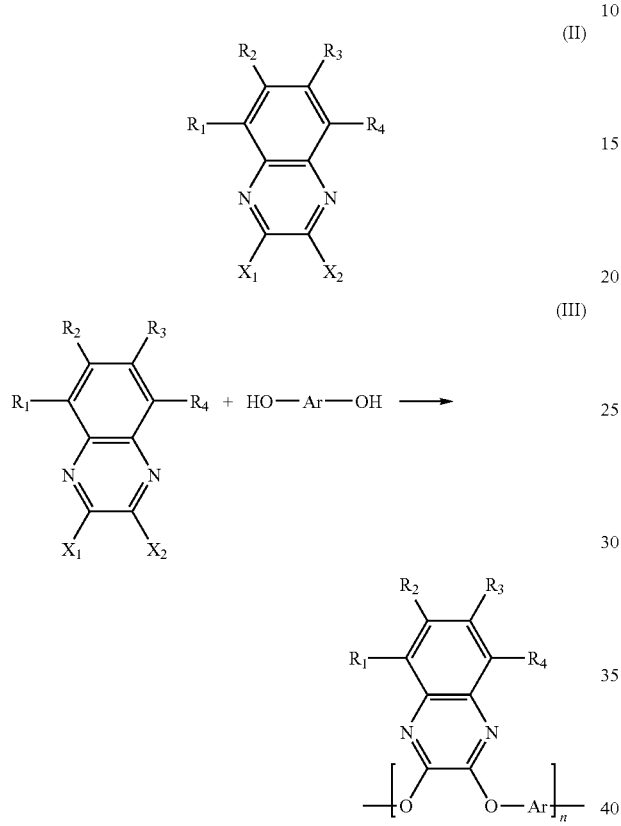

In Formulae I, II and III, "n" may be an integer from 1 to 10000, preferably from 50 to 200, $X_1$ and $X_2$ are independently a halogen (F, Cl, Br, I) or $NO_2$, $R_1$, $R_2$, $R_3$, $R_4$ may be hydrogen, methyl, $CF_3$, tert-butyl, benzoyl, benzenesulfonyl, a sulfonic acid salt, an aliphatic group, an alicyclic group, an aromatic group or any other chemical group stable and inert under the conditions of polymerization, and "Ar" represents a divalent aromatic radical derived from a bisphenol. In one particular example, HO—Ar—OH may be selected from the group consisting of:

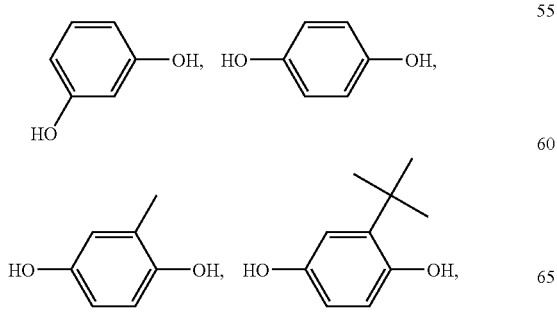

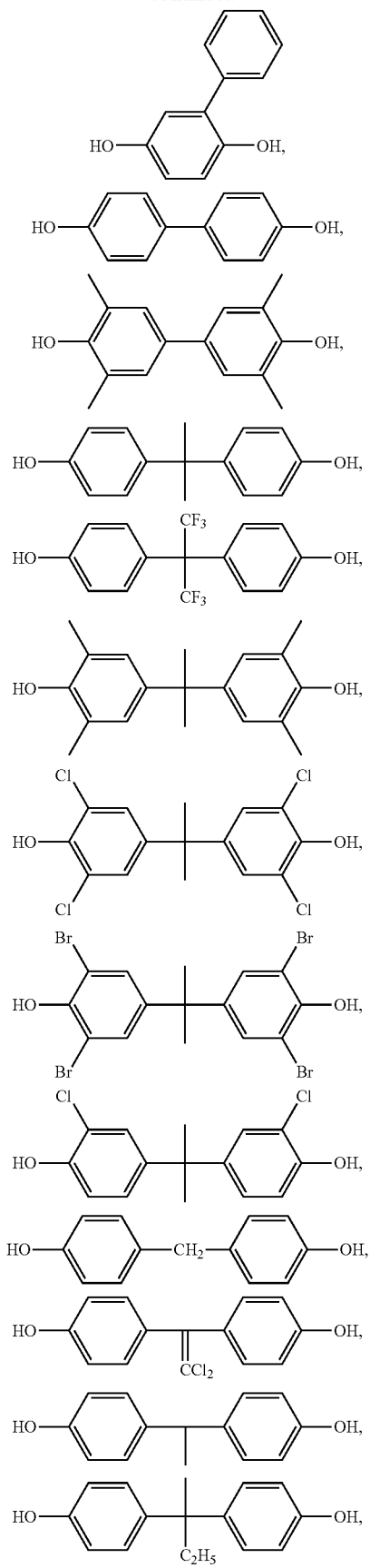

-continued
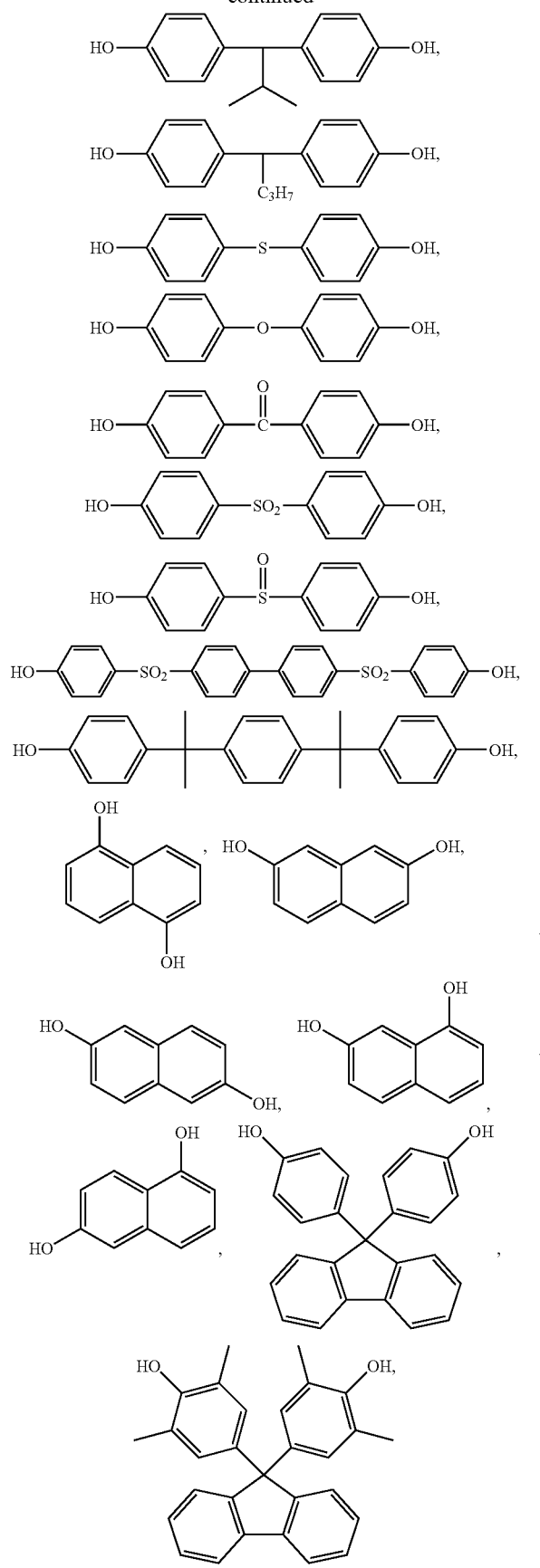
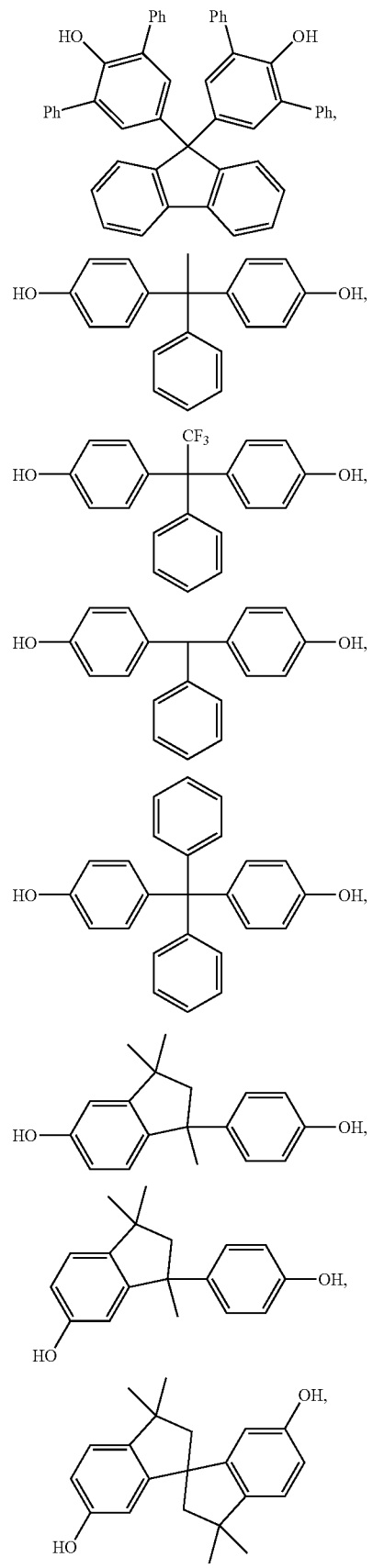

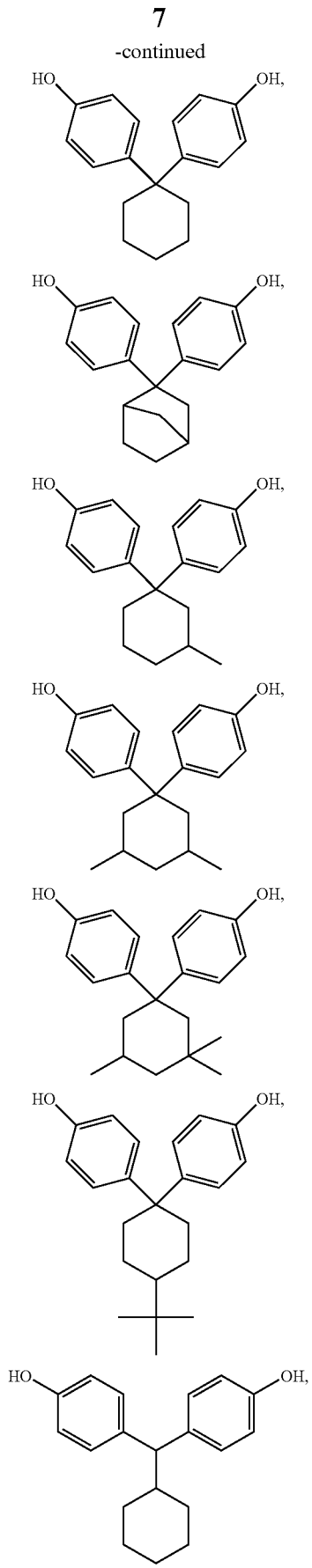

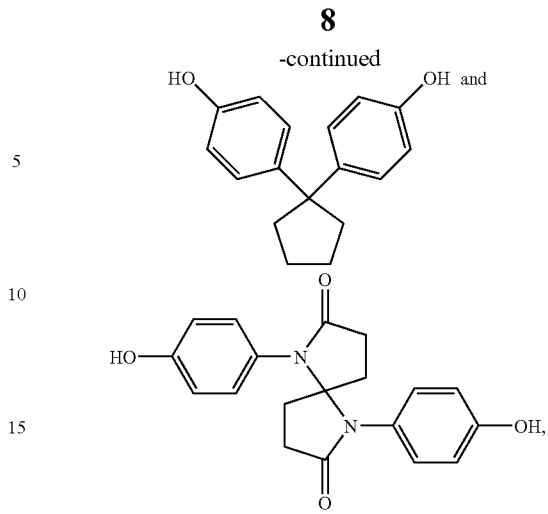

where Ph is a phenyl group. In another example, the bisphenol or a derivative thereof may be selected from the group consisting of bisphenol-A, 9,9-bis(4-hydroxyphenyl)fluorene, bisphenol-S and hexafluorobisphenol-A.

In one particular example, $X_1$ and $X_2$ are a halogen. In another example, $R_1$, $R_2$, $R_3$, $R_4$ are hydrogen. In still another example, the substituted or unsubstituted quinoxaline having replaceable groups at the 2,3 positions is 2,3-dichloroquinoxaline.

The melt-processable polyetherquinoxalines described herein can be prepared by aromatic nucleophilic substitution reaction under relatively mild conditions, have excellent thermal and mechanical properties, are organo-soluble, transparent and colorless thermoplastics. It is envisioned that these polyether quinoxalines may be used as thermoplastics in the areas of aerospace, automotive, high temperature adhesive, microelectronic, optical and membrane applications.

DETAILED DESCRIPTION OF THE INVENTION

The preparation of the polyetherquinoxalines of this invention, can be prepared by single step polymerization, two step polymerization, or heterogeneous polymerization using thermally stable phase transfer catalysts as described in the art. Substituted or unsubstituted quinoxalines with replaceable groups at the 2,3 positions ($X_1$ and $X_2$ in formula II), can be polymerized with a bisphenol or bisphenol derivative under aromatic nucleophilic substitution conditions, using a polar aprotic solvent under an inert atmosphere such as under argon or nitrogen, at a temperature between about 80° C. and about 250° C. In one example, the substituted or unsubstituted quinoxaline with replaceable groups at the 2,3 positions is 2,3 dichloroquinoxaline. In another example, the polar aprotic solvent is dimethylsulfoxide or dimethylacetamide. In still another example, the reaction temperature is below about 160° C. or between about 100° C. and about 160° C. In yet another example, the reaction temperature is between about 110° C. and about 130° C. It is also possible to use a gradual or stepwise heating of the polymerization mixture. The polymerization may be run under substantially anhydrous conditions and water can be removed azeotropically using chlorobenzene, toluene, xylene, etc., preferably toluene.

In a one-step process, the bisphenol or derivative thereof and activated dihalide or dinitro monomer are polymerized in a polar aprotic solvent using an alkali metal salt. The alkali metal salt may be potassium carbonate or sodium carbonate for example. In one example of the single step process, potassium carbonate ($K_2CO_3$) reacts with the phenol groups and forms a reactive phenoxide salt and potassium bicarbonate ($KHCO_3$). Over the range of 100-200° C., 2 moles of potassium bicarbonate will decompose into 1 mole of carbon dioxide, 1 mole of potassium carbonate and 1 mole of water. However, the inventors have found that at temperatures as low as 110° C., this decomposition of potassium bicarbonate to form additional reactive potassium carbonate is very slow. Therefore, to get high molecular weight polyetherquinoxalines described in this invention, it may be advantageous to use at least 100% excess of potassium carbonate in order to shorten the polymerization time to a practical level.

In a two step process, a bisphenol or bisphenol derivative is first reacted with an alkali metal salt to convert it into the more reactive bisphenol salt while the side product water is removed azeotropically. As described in the art, it is difficult to keep the dibasic salts of some bisphenols in the solution during polymerization. Two-step process has shorter polymerization times compared to the one step process and the final polymer has better quality such as less color. Color is believed to form due to side reactions and degradation of the polymerization solvent. Polyetherquinoxalines of this invention can also be prepared by a two step process, preferably in DMSO, but high quality polymer can also be obtained by single step process in short times under relatively mild conditions. It is envisioned that at these relatively low temperatures of polymerization, solvent degradation is minimized. Heterogeneous polymerization using a phase transfer catalyst can also be used for the preparation of polyetherquinoxalines described in this invention. Since relatively low temperatures are used in the preparation of polyetherquinoxalines of this invention, it is expected that the life time of the phase transfer catalyst will be increased.

The resulting polyetherquinoxalines are characterized by ether linkages at the 2 and 3 positions of the quinoxaline ring. Ether linkages increase the flexibility of the polymer chain, thus decreasing the glass transition, decreasing the melt viscosity, and improving the melt processability of the polymer. Different bisphenols and their copolymers can be used to control the glass transition of the polyetherquinoxalines.

The invention will be better understood by reference to the following examples which are included for the purpose of illustration and not limitation.

Comparative Example 1

Synthesis of 2,3-Dihydroxyquinoxaline

To a 2 L flask were added 280.0 g of oxalic acid dihydrate (2.221 moles) and then 1 L of distilled water. Then the mixture was heated to 90° C. After complete dissolution of oxalic acid, 400 mL of concentrated hydrochloric acid was added, followed by addition of 220.0 g of o-phenylenediamine (2.034 moles). The temperature was maintained at 90° C. for 30 minutes with continuous stirring. Off-white crystals were formed. After cooling to room temperature, the off-white crystals were collected by filtration, washed first with water, then with methanol and dried under reduced pressure to give 315.8 g (96%) of off-white needles: mp>350° C.

Comparative Example 2

Synthesis of 2,3-Dichloroquinoxaline 2,3-Dihydroxyquinoxaline (100.0 grams, 616.7 mmoles), thionyl chloride (350 mL) and dry DMF (5 mL) were added to a 500 mL flask. The flask was connected to a condenser, which was connected to a dry column. The mixture was gradually heated at reflux until the solid had completely dissolved, which took around 6 h. Then excess thionyl chloride was removed under reduced pressure to yield 120.8 g (98%) of crude 2,3-dichloroquinoxaline. Recrystallizations from toluene gave 86.5 g (72%) of white needles: mp 151-152° C.

Example 1

The Polymerization of 2,3-Dichloroquinoxaline with Bisphenol-A Using 100% Excess Potassium Carbonate In a 100 mL three necked flask equipped with a mechanical stirrer, a Claisen arm fitted with a nitrogen inlet tube, a Dean-Stark trap, a condenser and an exit gas bubbler were placed the following materials:
1.9904 g (10.000 mmole) of 2,3-dichloroquinoxaline,
2.2829 g (10.000 mmole) of bisphenol A,
2.7674 g (20.024 mmole) of anhydrous potassium carbonate,
16 mL of dimethylacetamide,
8 mL of toluene.

The flask was placed into an oil bath preheated to 122° C. The mixture was stirred under an argon atmosphere until a viscous solution was obtained, which took approximately 5 h. Final temperature of the oil bath was 127° C. During the polymerization, toluene was added in small amounts so as to maintain the azeotropic removal of water. The solution was diluted with 20 mL dimethylacetamide, and added to 600 mL 5:1 water:acetic acid mixture while stirring vigorously. The precipitate that formed was filtered, washed with water, and then methanol. The polymer was redissolved in 50 mL chloroform, acidified with 2-3 mL acetic acid and precipitated in 500 mL of methanol. The solid was collected by filtration, washed with methanol and stirred in boiling water for 1-2 h. The polymer was collected by filtration, washed with water, and then methanol, and dried in a vacuum oven at 120° C. to a constant weight. The yield of polymer was 3.27 grams. The polymer had an inherent viscosity of 0.66 g/dL (0.2 g/dL in n-methylpyrrolidinone at 30±0.1° C.). Glass transition of the polymer was 193° C. 2.0 grams of polymer was compression molded at 300° C. under 1000 psi for 5 min to give slightly yellow, transparent and tough film. A thin film of this polymer was cast from chloroform and subjected to preliminary stress-strain measurements according to ASTM D882. The tensile strength of the film was 104 MPa and its tensile modulus was 3.3 GPa.

Example 2

The Polymerization of 2,3-Dichloroquinoxaline with Bisphenol-A Using 10% Excess Potassium Carbonate In a 100 mL three necked flask equipped with a mechanical stirrer, a Claisen arm fitted with a nitrogen inlet tube, a Dean-Stark trap, a condenser and an exit gas bubbler were placed the following materials:
3.9808 g (20.000 mmole) of 2,3-dichloroquinoxaline,
4.5657 g (20.000 mmole) of bisphenol A,
3.0437 g (22.022 mmole) of anhydrous potassium carbonate,
28 mL of dimethylacetamide,
10 mL of toluene.

The flask was placed into an oil bath preheated to 122° C. The mixture was stirred under an argon atmosphere for 24 h without any increase in viscosity of the solution. The final temperature of the oil bath was 132° C. During the polymerization, toluene was added in small amounts so as to maintain the azeotropic removal of water. The solution added to 600 mL of 5:1 water:acetic acid mixture while stirring vigorously. The powder precipitate that was formed was collected by filtration, washed with water, and then methanol. The polymer was redissolved in 50 mL chloroform, acidified with 2-3 mL acetic acid and precipitated in 500 mL of methanol. The solid was collected by filtration, washed with methanol and stirred in boiling water for 1-2 h. The polymer was collected by filtration, washed with water, then methanol, and dried in a vacuum oven at 120° C. to a constant weight. The yield of polymer was 4.12 grams. The product melted in the drying step in the vacuum oven at 120° C.

Example 3

The Polymerization of 2,3-Dichloroquinoxaline with 9,9'-Bis(4-hydroxyphenyl)fluorine In a 100 mL three necked flask equipped with a mechanical stirrer, a Claisen arm fitted with a nitrogen inlet tube, a Dean-Stark trap, a condenser and an exit gas bubbler were placed the following materials:
    1.9904 g (10.000 mmole) of 2,3-dichloroquinoxaline,
    3.5041 g (10.000 mmole) of 9,9'-bis(4-hydroxyphenyl)fluorene,
    2.7664 g (20.017 mmole) of anhydrous potassium carbonate,
    24 mL of dimethylacetamide,
    10 mL of toluene.

The flask was placed into an oil bath preheated to 114° C. The mixture was stirred under an argon atmosphere until a viscous solution was obtained, which took approximately 5 h. The final temperature of the oil bath was 130° C. During the polymerization, toluene was added in small amounts so as to maintain the azeotropic removal of water. The solution was diluted with 20 mL dimethylacetamide, and added to 600 mL 5:1 water:acetic acid mixture while stirring vigorously. The precipatate that formed was collected by filtration, washed with water, and then methanol. The polymer was redissolved in 100 mL chloroform, acidified with 2-3 mL acetic acid and precipitated in 1000 mL of methanol. The solid was collected by filtration, washed with methanol and stirred in boiling water for 1-2 h. The polymer was collected by filtration, washed water, and then methanol, and dried in a vacuum oven at 120° C. to a constant weight. The yield of polymer was 4.39 g. The polymer had an inherent viscosity of 0.57 g/dL (0.2 g/dL in n-methylpyrrolidinone at 30±0.1° C.). Glass transition of the polymer was 279° C.

Example 6

The polymerization of 2,3-Dichloroquinoxaline with Bisphenol-S

In a 100 mL three necked flask equipped with a mechanical stirrer, a Claisen arm fitted with a nitrogen inlet tube, a Dean-Stark trap, a condenser and an exit gas bubbler were placed the following materials:
    1.9904 g (10.000 mmole) of 2,3-dichloroquinoxaline,
    2.5027 g (10.000 mmole) of bisphenol-S,
    2.7681 g (20.029 mmole) of anhydrous potassium carbonate,
    19 mL of dimethylacetamide,
    11 mL of toluene.

The flask was placed into an oil bath preheated to 120° C. The mixture was stirred under an argon atmosphere for 6 h. The final temperature of the oil bath was 130° C. During the polymerization, toluene was added in small amounts so as to maintain the azeotropic removal of water. The solution diluted with 20 mL dimethylacetamide, and then added to 800 mL 7:1 water:acetic acid mixture while stirring vigorously. The precipatate that was formed collected by filtration, washed with water, and then methanol. The polymer redissolved in 50 mL dimethylacetamide, acidified with 2-3 mL acetic acid and precipitated in 1000 mL of methanol. The solid was collected by filtration, washed with methanol and stirred in boiling water for 1-2 h. The polymer was collected by filtration, washed with water, and then methanol, and dried in a vacuum oven at 120° C. to a constant weight. The yield of polymer was 3.48 grams. The polymer had an inherent viscosity of 0.67 g/dL (0.2 g/dL in n-methylpyrrolidinone at 30±0.1° C.). Glass transition of the polymer was 228° C.

Example 7

The Polymerization of 2,3-Dichloroquinoxaline with Hexafluorobisphenol-A

In a 100 mL three necked flask equipped with a mechanical stirrer, a Claisen arm fitted with a nitrogen inlet tube, a Dean-Stark trap, a condenser and an exit gas bubbler were placed the following materials:
    1.9904 g (10.000 mmole) of 2,3-dichloroquinoxaline,
    3.3623 g (10.000 mmole) of hexafluorobisphenol-A,
    2.7699 g (20.042 mmole) of anhydrous potassium carbonate,
    23 mL of dimethylacetamide,
    10 mL of toluene.

The flask was placed into an oil bath preheated to 120° C. The mixture was stirred under an argon atmosphere for 8 h. Final temperature of the oil bath was 128° C. During the polymerization, toluene was added in small amounts so as to maintain the azeotropic removal of water. The solution was diluted with 20 mL dimethylacetamide, and added to 600 mL 5:1 water:acetic acid mixture while stirring vigorously. The precipitate that formed was collected by filtration, washed with water, and then methanol. The polymer was redissolved in 50 mL tetrahydrofuran, acidified with 2-3 mL acetic acid and precipitated in 500 mL of methanol. The solid was collected by filtration, washed with methanol and stirred in boiling water for 1-2 h. The polymer was collected by filtration, washed with water, and then methanol, and dried in a vacuum oven at 120° C. to a constant weight. The yield of polymer was 4.39 grams. The polymer had an inherent viscosity of 0.64 g/dL (0.2 g/dL in n-methylpyrrolidinone at 30±0.1° C.). Glass transition of the polymer was 191° C.

Example 8

The Polymerization of 2,3-Dichloroquinoxaline with Hydroquinone

In a 100 mL three necked flask equipped with a mechanical stirrer, a Claisen arm fitted with a nitrogen inlet tube, a Dean-Stark trap, a condenser and an exit gas bubbler were placed the following materials:
    1.9904 g (10.000 mmole) of 2,3-dichloroquinoxaline,
    1.1011 g (10.000 mmole) of hydroquinone,
    2.7692 g (20.037 mmole) of anhydrous potassium carbonate,
    12 mL of dimethylacetamide,
    10 mL of toluene.

The flask was placed into an oil bath preheated to 120° C. The mixture was stirred under an argon atmosphere for 4 h. The final temperature of the oil bath was 130° C. Toluene was added in small amounts so as to maintain the azeotropic removal of water. During polymerization, white powders formed. The solution was diluted with 20 mL dimethylacetamide, and then added to 600 mL 5:1 water:acetic acid mixture while stirring vigorously. The white powder was collected by filtration, washed with water and then methanol, and dried in a vacuum oven at 80° C. The yield of polymer was 2.17 g.

Example 9

The Polymerization of 2,3-Dichloroquinoxaline with 4,4'-Biphenol

In a 100 mL three necked flask equipped with a mechanical stirrer, a Claisen arm fitted with a nitrogen inlet tube, a Dean-Stark trap, a condenser and an exit gas bubbler were placed the following materials:
  1.9904 g (10.000 mmole) of 2,3-dichloroquinoxaline,
  1.8621 g (10.000 mmole) of 4,4'-biphenol,
  2.7683 g (20.030 mmole) of anhydrous potassium carbonate,
  16 mL of dimethylacetamide,
  10 mL of toluene.

The flask was placed into an oil bath preheated to 122° C. The mixture was stirred under an argon atmosphere for 6 h. The final temperature of the oil bath was 130° C. Toluene was added in small amounts so as to maintain the azeotropic removal of water. During polymerization, white powders formed. The solution diluted with 20 mL dimethylacetamide, and then added to 600 mL 5:1 water:acetic acid mixture while stirring vigorously. The white powder was collected by filtration, washed with water and then methanol, and dried in a vacuum oven at 80° C. The yield of polymer was 2.92 g.

Example 10

The Polymerization of 2,3-Dichloroquinoxaline with Bisphenol A (50%) and Hydroquinone (50%)

In a 100 mL, three-necked flask equipped with a mechanical stirrer, a Claisen arm fitted with a nitrogen inlet tube, a Dean-Stark trap, a condenser and an exit gas bubbler were placed the following materials:
  1.9904 g (10.000 mmole) of 2,3-dichloroquinoxaline,
  1.1414 g (5.0000 mmole) of bisphenol A,
  0.5506 g (5.000 mmole) of hydroquinone,
  2.7649 g (20.006 mmole) of anhydrous potassium carbonate,
  15 mL of dimethylacetamide, 8 mL of toluene.

The flask was placed into an oil bath preheated to 122° C. The mixture was stirred under an argon atmosphere until a viscous solution in obtained, which took approximately 5 h. The final temperature of the oil bath was 130° C. During the polymerization, toluene was added in small amounts so as to maintain the azeotropic removal of water. The solution diluted with 20 mL dimethylacetamide, and then added to 600 mL 5:1 water:acetic acid mixture while stirring vigorously. The precipatate that formed was collected by filtration, washed with water, and then methanol. The polymer was redissolved in 70 mL chloroform, acidified with 2-3 mL acetic acid and precipitated in 500 mL of methanol. The solid was collected by filtration, washed with methanol and stirred in boiling water for 1-2 h. The polymer was collected by filtration, washed with water, and then methanol, and dried in a vacuum oven at 120° C. to a constant weight. The yield of polymer was 2.83 grams. The polymer had an inherent viscosity of 1.01 g/dL (0.2 g/dL in n-methylpyrrolidinone at 30±0.1° C.). Glass transition of the polymer was 199° C.

Example 11

The Polymerization of 2,3-Dichloroquinoxaline with Bisphenol A (50%) and 4, 4'-Biphenol (50%)

In a 100 mL three necked flask equipped with a mechanical stirrer, a Claisen arm fitted with a nitrogen inlet tube, a Dean-Stark trap, a condenser and an exit gas bubbler were placed the following materials:
  3.9808 g (20.000 mmole) of 2,3-dichloroquinoxaline,
  2.2829 g (10.000 mmole) of bisphenol A,
  1.8621 g (10.000 mmole) of 4,4'-biphenol,
  5.5354 g (40.052 mmole) of anhydrous potassium carbonate,
  34 mL of dimethylacetamide,
  17 mL of toluene.

The flask was placed into an oil bath preheated to 122° C. The mixture was stirred under an argon atmosphere for 7 h. The final temperature of the oil bath was 132° C. Toluene was added in small amounts so as to maintain the azeotropic removal of water. During polymerization, white powders formed. The solution diluted with 20 mL dimethylacetamide, and then added to 600 mL 5:1 water:acetic acid mixture while stirring vigorously. The white powder was collected by filtration, washed with water and then methanol, and dried in a vacuum oven at 80° C. The yield of polymer was 6.27 g.

The precipitate was a powder, which is an indication of low molecular weight.

Based upon the foregoing disclosure, it should now be apparent that a polyetherquinoxaline and a method for synthesizing a polyetherquinoxaline is provided. It is, therefore, to be understood that any variations evident fall within the scope of the claimed invention and thus, the selection of specific component elements can be determined without departing from the spirit of the invention herein disclosed and described.

The invention claimed is:

1. A method for synthesizing a polyetherquinoxaline, the method comprising contacting a substituted or unsubstituted quinoxaline having replaceable groups at the 2,3 positions with a bisphenol or a derivative thereof under aromatic nucleophilic substitution reaction conditions.

2. The method of claim 1, wherein substituted or unsubstituted quinoxaline having replaceable groups at the 2,3 positions has the structure of formula II

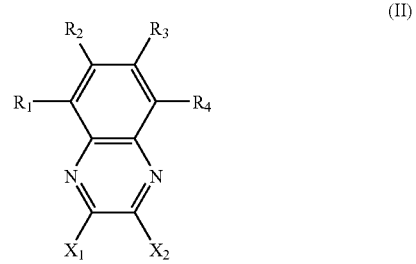

(II)

wherein $X_1$ and $X_2$ are independently a halogen or $NO_2$, $R_1, R_2, R_3, R_4$ are independently hydrogen, methyl, $CF_3$, tert-butyl, benzoyl, benzenesulfonyl, a sulfonic acid salt, an aliphatic group, an alicyclic group, or an aryl group.

3. The method of claim 2, wherein $X_1$ and $X_2$ are independently a halogen.

4. The method of claim 3, wherein the substituted or unsubstituted quinoxaline having replaceable groups at the 2, 3 positions is 2,3-dichloroquinoxaline.

5. The method of claim 4, wherein the reaction conditions include using a polar aprotic solvent under an inert atmosphere at a temperature between about 80° C. and about 250° C.

6. The method of claim 5, wherein the temperature is less than about 160° C.

7. The method of claim 5, wherein the bisphenol or a derivative thereof is selected from the group consisting of bisphenol-A, 9,9-bis(4-hydroxyphenyl)fluorene, bisphenol-S and hexafluorobisphenol-A.

8. The method of claim 4, wherein the bisphenol or a derivative thereof is selected from the group consisting of bisphenol-A, 9,9-bis(4-hydroxyphenyl)fluorene, bisphenol-S and hexafluorobisphenol-A.

9. The method of claim 1, wherein the reaction conditions include using a polar aprotic solvent under an inert atmosphere at a temperature between about 80° C. and about 250° C.

10. The method of claim 9, wherein the temperature is less than about 160° C.

11. The method of claim 10, wherein the bisphenol or a derivative thereof is selected from the group consisting of bisphenol-A, 9,9-bis(4-hydroxyphenyl)fluorene, bisphenol-S and hexafluorobisphenol-A.

12. The method of claim 11, wherein $R_1$, $R_2$, $R_3$, and $R_4$ are hydrogen.

13. The method of claim 2, wherein the reaction conditions include using a polar aprotic solvent under an inert atmosphere at a temperature between about 80° C. and about 250° C.

14. The method of claim 13, wherein $R_1$, $R_2$, $R_3$, and $R_4$ are hydrogen.

15. The method of claim 14, wherein the reaction conditions include a temperature less than about 160° C.

16. A polyetherquinoxaline comprising a plurality of quinoxaline groups joined by ether linkages at the 2 and 3 positions of the quinoxaline groups.

17. The polyetherquinoxaline according to claim 16, having a formula represented as

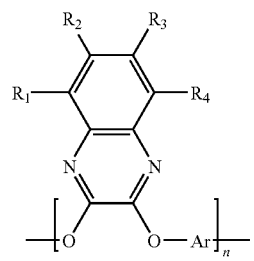

wherein "n" is an integer from 1 to 10000, and $R_1$, $R_2$, $R_3$, $R_4$ are independently hydrogen, methyl, $CF_3$, tert-butyl, benzoyl, benzenesulfonyl, a sulfonic acid salt, an aliphatic group, an alicyclic group, or an aryl group, and Ar is an aromatic radical.

18. The polyetherquinoxaline according to claim 17, wherein Ar is a divalent aromatic radical derived from bisphenol-A, 9,9-bis(4-hydroxyphenyl)fluorene, bisphenol-S or hexafluorobisphenol-A.

19. The polyetherquinoxaline according to claim 18, wherein $R_1$, $R_2$, $R_3$, and $R_4$ are each hydrogen.

20. The polyetherquinoxaline according to claim 17, wherein $R_1$, $R_2$, $R_3$, $R_4$ are each hydrogen.

* * * * *